United States Patent
McBroom et al.

(10) Patent No.: US 8,795,303 B2
(45) Date of Patent: *Aug. 5, 2014

(54) MULTI-MATERIAL ABRADING HEAD FOR ATHERECTOMY DEVICES HAVING LATERALLY DISPLACED CENTER OF MASS

(75) Inventors: Jeffrey A. McBroom, Champlin, MN (US); Larry A. Waller, Minneapolis, MN (US)

(73) Assignee: Cardiovascular Systems, Inc., St. Paul, MN (US)

( * ) Notice: Subject to any disclaimer, the term of this patent is extended or adjusted under 35 U.S.C. 154(b) by 400 days.

This patent is subject to a terminal disclaimer.

(21) Appl. No.: 12/363,914

(22) Filed: Feb. 2, 2009

(65) Prior Publication Data
US 2010/0198239 A1 Aug. 5, 2010

(51) Int. Cl.
*A61B 17/22* (2006.01)
*A61B 17/3207* (2006.01)
*A61B 17/32* (2006.01)

(52) U.S. Cl.
CPC ............ *A61B 17/320758* (2013.01); *A61B 2017/320733* (2013.01); *A61B 17/3207* (2013.01); *A61B 2017/320004* (2013.01)
USPC ....................................................... 606/159

(58) Field of Classification Search
USPC ......... 606/108, 159, 167, 170, 180, 110, 112, 606/114, 127, 128; 604/22
See application file for complete search history.

(56) References Cited

U.S. PATENT DOCUMENTS

| | | | |
|---|---|---|---|
| 1,881,821 A | 10/1932 | McCracken | |
| 2,221,195 A | 11/1940 | Ketsios | |
| 2,348,132 A | 5/1944 | Hyland | |
| 3,199,933 A * | 8/1965 | Rogerson et al. | 384/398 |
| 3,507,695 A * | 4/1970 | Sawyer | 134/1 |
| 4,126,910 A | 11/1978 | Beer | |
| 4,181,998 A | 1/1980 | Nelson | |
| 4,445,059 A | 4/1984 | Corbach et al. | |
| 4,732,154 A | 3/1988 | Shiber | |
| 4,795,438 A | 1/1989 | Kensey et al. | |
| 4,811,735 A | 3/1989 | Nash et al. | |
| 4,990,134 A | 2/1991 | Auth | |
| 5,030,201 A | 7/1991 | Palestrant | |
| 5,087,265 A | 2/1992 | Summers | |

(Continued)

FOREIGN PATENT DOCUMENTS

WO  WO2006/126065  11/2006

*Primary Examiner* — David Eastwood
(74) *Attorney, Agent, or Firm* — Winthrop & Weinstine, P.A.

(57) ABSTRACT

An abrading head for a high-speed rotation atherectomy device is disclosed. The head has its center of mass laterally displaced from the rotational axis of the drive shaft. As the drive shaft spins, centrifugal force forces the abrading head radially outward. At high speeds, and the abrasive portion of the head may subtend an abrading cylinder larger than at low speeds or at rest. The abrading head has two components, each having a different density. The connection portion may be an incomplete cylinder, which fastens onto the drive shaft, and may be a relatively low density metal, such as stainless steel. The eccentric portion may be a relatively high density metal, such as tungsten or tantalum, and is attached to the connection portion. The eccentric portion has all or most of its mass on one side of the rotation axis of the drive shaft, providing a larger separation between the center of mass of the abrading head and the rotational axis of the drive shaft than if the abrading head were made from only one material.

18 Claims, 8 Drawing Sheets

(56) References Cited

U.S. PATENT DOCUMENTS

| | | | | |
|---|---|---|---|---|
| 5,100,425 | A | 3/1992 | Fischell et al. | |
| 5,222,959 | A | 6/1993 | Anis | |
| 5,242,461 | A | 9/1993 | Kortenbach et al. | |
| 5,314,438 | A | 5/1994 | Shturman | |
| 5,318,576 | A | 6/1994 | Plassche, Jr. et al. | |
| 5,376,100 | A | 12/1994 | Lefebvre | |
| 5,403,334 | A | 4/1995 | Evans et al. | |
| 5,632,755 | A | 5/1997 | Nordgren et al. | |
| 5,643,297 | A | 7/1997 | Nordgren et al. | |
| 5,643,298 | A | 7/1997 | Nordgren et al. | |
| 5,681,336 | A * | 10/1997 | Clement et al. | 606/159 |
| 5,746,758 | A | 5/1998 | Nordgren et al. | |
| 5,968,064 | A | 10/1999 | Selmon et al. | |
| 6,015,420 | A * | 1/2000 | Wulfman et al. | 606/168 |
| 6,132,444 | A | 10/2000 | Shturman et al. | |
| 6,146,395 | A | 11/2000 | Kanz et al. | |
| 6,416,526 | B1 | 7/2002 | Wyzgala et al. | |
| 6,436,111 | B1 | 8/2002 | Kadavy et al. | |
| 6,451,037 | B1 | 9/2002 | Chandrasekaran et al. | |
| 6,467,121 | B1 | 10/2002 | Franzino et al. | |
| 6,494,890 | B1 * | 12/2002 | Shturman et al. | 606/159 |
| 6,565,588 | B1 | 5/2003 | Clement et al. | |
| 6,596,005 | B1 | 7/2003 | Kanz et al. | |
| 6,685,718 | B1 | 2/2004 | Wyzgala et al. | |
| 6,818,001 | B2 | 11/2004 | Wulfman et al. | |
| 7,252,674 | B2 | 8/2007 | Wyzgala et al. | |
| 8,348,965 | B2 * | 1/2013 | Prudnikov et al. | 606/159 |
| 2001/0018596 | A1 | 8/2001 | Selmon et al. | |
| 2002/0077638 | A1 | 6/2002 | Kadavy et al. | |
| 2002/0147458 | A1 | 10/2002 | Hiblar et al. | |
| 2002/0151825 | A1 * | 10/2002 | Rubenchik et al. | 601/2 |
| 2003/0084996 | A1 * | 5/2003 | Alberg et al. | 156/324 |
| 2003/0125756 | A1 * | 7/2003 | Shturman et al. | 606/159 |
| 2003/0139751 | A1 * | 7/2003 | Evans et al. | 606/127 |
| 2003/0199889 | A1 | 10/2003 | Kanz et al. | |
| 2004/0006358 | A1 | 1/2004 | Wulfman et al. | |
| 2004/0054368 | A1 | 3/2004 | Truckai et al. | |
| 2004/0158270 | A1 * | 8/2004 | Wyzgala et al. | 606/170 |
| 2005/0149084 | A1 | 7/2005 | Kanz et al. | |
| 2008/0306498 | A1 | 12/2008 | Thatcher et al. | |
| 2009/0018564 | A1 * | 1/2009 | Shturman | 606/159 |

* cited by examiner

MULTI-MATERIAL ABRADING HEAD FOR ATHERECTOMY DEVICES HAVING LATERALLY DISPLACED CENTER OF MASS

BACKGROUND OF THE INVENTION

1. Field of the Invention

The invention relates to devices and methods for removing tissue from body passageways, such as removal of atherosclerotic plaque from arteries, utilizing a high-speed rotational atherectomy device.

2. Description of the Related Art

A variety of techniques and instruments have been developed for use in the removal or repair of tissue in arteries and similar body passageways. A frequent objective of such techniques and instruments is the removal of atherosclerotic plaques in a patient's arteries. Atherosclerosis is characterized by the buildup of fatty deposits (atheromas) in the intimal layer (under the endothelium) of a patient's blood vessels. Very often over time, what initially is deposited as relatively soft, cholesterol-rich atheromatous material hardens into a calcified atherosclerotic plaque. Such atheromas restrict the flow of blood, and therefore often are referred to as stenotic lesions or stenoses, the blocking material being referred to as stenotic material. If left untreated, such stenoses can cause angina, hypertension, myocardial infarction, strokes and the like.

Rotational atherectomy procedures have become a common technique for removing such stenotic material. Such procedures are used most frequently to initiate the opening of calcified lesions in coronary arteries. Most often the rotational atherectomy procedure is not used alone, but is followed by a balloon angioplasty procedure, which, in turn, is very frequently followed by placement of a stent to assist in maintaining patentcy of the opened artery. For non-calcified lesions, balloon angioplasty most often is used alone to open the artery, and stents often are placed to maintain patentcy of the opened artery. Studies have shown, however, that a significant percentage of patients who have undergone balloon angioplasty and had a stent placed in an artery experience stent restenosis, which is a blockage of the stent that most frequently develops over a period of time as a result of excessive growth of scar tissue within the stent. In such situations an atherectomy procedure is the preferred procedure to remove the excessive scar tissue from the stent (balloon angioplasty being not very effective within the stent), thereby restoring the patentcy of the artery.

Several kinds of rotational atherectomy devices have been developed for attempting to remove stenotic material. In one type of device, such as that shown in U.S. Pat. No. 4,990,134, issued to Auth, a burr covered with an abrasive abrading material such as diamond particles is carried at the distal end of a flexible drive shaft. The burr is rotated at high speeds (typically, e.g., in the range of about 150,000-190,000 revolutions per minute) while it is advanced across the stenosis. As the burr is removing stenotic tissue, however, it blocks blood flow. Once the burr has been advanced across the stenosis, the artery will have been opened to a diameter equal to or only slightly larger than the maximum outer diameter of the burr. Frequently more than one size burr must be utilized to open an artery to the desired diameter.

U.S. Pat. No. 5,314,438, issued to Shturman, discloses another atherectomy device having a drive shaft with a section of the drive shaft having an enlarged diameter, at least a segment of this enlarged surface being covered with an abrasive material to define an abrasive segment of the drive shaft. When rotated at high speeds, the abrasive segment is capable of removing stenotic tissue from an artery. Though this atherectomy device possesses certain advantages over the Auth device due to its flexibility, it also is capable only of opening an artery to a diameter about equal to the diameter of the enlarged abrading surface of the drive shaft since the device is not eccentric in nature.

U.S. Pat. No. 6,494,890, issued to Shturman, discloses an atherectomy device having a drive shaft with an enlarged eccentric section, wherein at least a segment of this enlarged section is covered with an abrasive material. When rotated at high speeds, the abrasive segment is capable of removing stenotic tissue from an artery. The device is capable of opening an artery to a diameter that is larger than the resting diameter of the enlarged eccentric section due, in part, to the orbital rotational motion during high speed operation. Since the enlarged eccentric section includes drive shaft wires that are not bound together, the enlarged eccentric section of the drive shaft may flex during placement within the stenosis or during high speed operation. This flexion allows for a larger diameter opening during high speed operation, but may also provide less control than desired over the diameter of the artery actually abraded. In addition, some stenotic tissue may block the passageway so completely that the Shturman device cannot be placed therethrough. Since Shturman requires that the enlarged eccentric section of the drive shaft be placed within the stenotic tissue to achieve abrasion, it will be less effective in cases where the enlarged eccentric section is prevented from moving into the stenosis. The disclosure of U.S. Pat. No. 6,494,890 is hereby incorporated by reference in its entirety.

U.S. Pat. No. 5,681,336, issued to Clement, provides an eccentric tissue removing burr with a coating of abrasive particles secured to a portion of its outer surface by a suitable binding material. This construction is limited, however because, as Clement explains at Col. 3, lines 53-55, that the asymmetrical burr is rotated at "lower speeds than are used with high speed ablation devices, to compensate for heat or imbalance." That is, given both the size and mass of the solid burr, it is infeasible to rotate the burr at the high speeds used during atherectomy procedures, i.e., 20,000-200,000 revolutions per minute. Essentially, the center of mass offset from the rotational axis of the drive shaft would result in development of significant centrifugal force, exerting too much pressure on the wall of the artery and creating too much heat and excessively large particles.

Commonly assigned U.S. patent application Ser. No. 11/761,128, entitled Eccentric Abrading Head for High-Speed Rotational Atherectomy Devices, discloses certain embodiments of an eccentric abrading head. Specifically, application '128 discloses a flexible, elongated, rotatable drive shaft with at least one flexible, or non-flexible, eccentric enlarged abrading head attached thereto. In application '128, at least part of the eccentric enlarged cutting head has a tissue removing surface, which is typically an abrasive surface. In certain embodiments, the abrading head will be at least partially hollow. When placed within an artery against stenotic tissue and rotated at sufficiently high speeds the eccentric nature of the enlarged cutting head causes the cutting head and drive shaft to rotate in such a fashion as to open the stenotic lesion to a diameter substantially larger than the outer diameter of the enlarged cutting head. Preferably the eccentric enlarged cutting head has a center of mass spaced radially from the rotational axis of the drive shaft, facilitating the ability of the device to open the stenotic lesion to a diameter substantially larger than the outer diameter of the enlarged cutting head when operated at high speeds.

The eccentric abrading head disclosed in application Ser. No. 11/761,128 is made primarily from a single material, neglecting hollow portions and the abrasive coating on the exterior of the head. In application '128, the shifting of the center of mass away from the rotational axis of the drive shaft is accomplished primarily by the placement of material. In other words, to move the center of mass off axis, one places more material on one side of the rotational axis than the other, and/or adds holes or voids in the abrading head where appropriate. The disclosure of application Ser. No. 11/761,128 is incorporated herein in its entirety.

For a particular abrading head geometry, such as of the type disclosed in application '128, it may be desirable to reduce the rotational speed at which the abrading head traces out a particular cutting diameter. Such a reduction in required rotational speed can reduce the cost and complexity of the device, which is also desirable.

For the abrading heads disclosed above, one may reposition the center of mass by adding or subtracting material at certain locations. If one wishes additionally to maintain a particular abrading head geometry, thereby fixing the external dimensions of the abrading head, one may remove material from locations inside the head, or, equivalently, add hollow portions inside the head. This has the drawback of reducing both the total mass of the abrading head and the rotational inertia of the abrading head.

Accordingly, there exists a need for an improved abrading head, which can trace out a particular cutting diameter with a reduced rotational speed, without substantially altering the external dimensions, reducing the mass, or reducing the rotational inertia of the abrading head.

BRIEF SUMMARY OF THE INVENTION

An embodiment is a high-speed rotational atherectomy device for opening a stenosis in an artery having a given diameter, comprising: a guide wire having a maximum diameter less than the diameter of the artery; a flexible, elongated, rotatable drive shaft advanceable over the guide wire, the drive shaft having a rotational axis and having a controllable drive shaft rotation speed; at least one eccentric abrading head attached to the drive shaft, the at least one eccentric abrading head comprising: a connecting portion fixedly attached to and at least partially surrounding the drive shaft and being formed from a connecting portion material; an eccentric portion fixedly attached to and at least partially surrounding the connecting portion and formed from a eccentric portion material different from the connecting portion material, the eccentric portion including a proximal portion, a central portion adjacent to the proximal portion, and a distal portion adjacent to the central portion opposite the proximal portion; and an abrasive portion disposed on an exterior surface of the central portion. The eccentric portion material is more dense than the connecting portion material.

An additional embodiment is a method for opening a stenosis in an artery having a given diameter, comprising: providing a guide wire having a maximum diameter less than the diameter of the artery; advancing the guide wire into the artery to a position proximal to the stenosis; providing a flexible elongated, rotatable drive shaft advanceable over the guide wire, the drive shaft having a rotational axis; providing at least one eccentric abrading head attached to the drive shaft, the abrading head including: a connecting portion at least partially surrounding the drive shaft; an eccentric portion at least partially surrounding the connecting portion; and an abrasive portion disposed on a portion of an external face of the eccentric portion; wherein the connecting portion and the eccentric portion are made from different materials, and wherein the eccentric portion is more dense than the connecting portion; advancing the drive shaft over the guide wire wherein the at least one eccentric abrading head is adjacent the stenosis; rotating the drive shaft and attached at least one eccentric abrading head at a speed between 20,000 and 200,000 rpm; creating an orbital path traversed by the at least one eccentric abrading head; and abrading the stenosis with the at least one eccentric abrading head.

A further embodiments is a high-speed rotational atherectomy device for opening a stenosis in an artery having a given diameter, comprising: a guide wire having a maximum diameter less than the diameter of the artery; a flexible, elongated, rotatable drive shaft advanceable over the guide wire, the drive shaft having a rotational axis and having a controllable drive shaft rotation speed; at least one non-eccentric abrading head attached to the drive shaft, the at least one non-eccentric abrading head comprising: a connecting portion fixedly attached to and at least partially surrounding the drive shaft and being formed from a connecting portion material; a non-eccentric portion fixedly attached to and at least partially surrounding the connecting portion and formed from a non-eccentric portion material different from the connecting portion material, the non-eccentric portion including a proximal portion, a central portion adjacent to the proximal portion, and a distal portion adjacent to the central portion opposite the proximal portion; and an abrasive portion disposed on an exterior surface of the central portion. The non-eccentric portion material is more dense than the connecting portion material.

DETAILED DESCRIPTION OF THE INVENTION

An atherectomy device with a rotating abrasive head removes plaque from the inside of artery walls. The abrasive head has its center of mass laterally displaced from the rotational axis of the device, so that when the device spins, centrifugal force pushes the abrasive head outward, away from the rotational axis. In this manner, the abrasive head, when spinning, may trace out a cutting radius that exceeds its own size. This may be referred to as an "orbit", with the abrasive head following an "orbital motion". The abrasive head may include a rigid crown that is attached to the drive shaft. The rigid crown may be made from two or more different materials, such as metals, with different densities. The less dense material may be used to attach the crown to the drive shaft, while the more dense material may be used at the periphery of the crown. For a particular geometry, compared to a crown made from a single material, the center of mass is moved outwards, thereby creating more rotational inertia and desirably causing larger orbits at lower speeds.

The preceding paragraph is merely a generalized summary of the disclosure, and should not be construed as limiting in any way. A more detailed description of the multi-material crown is presented below, following a description of a generalized rotational atherectomy device.

Figure 1:
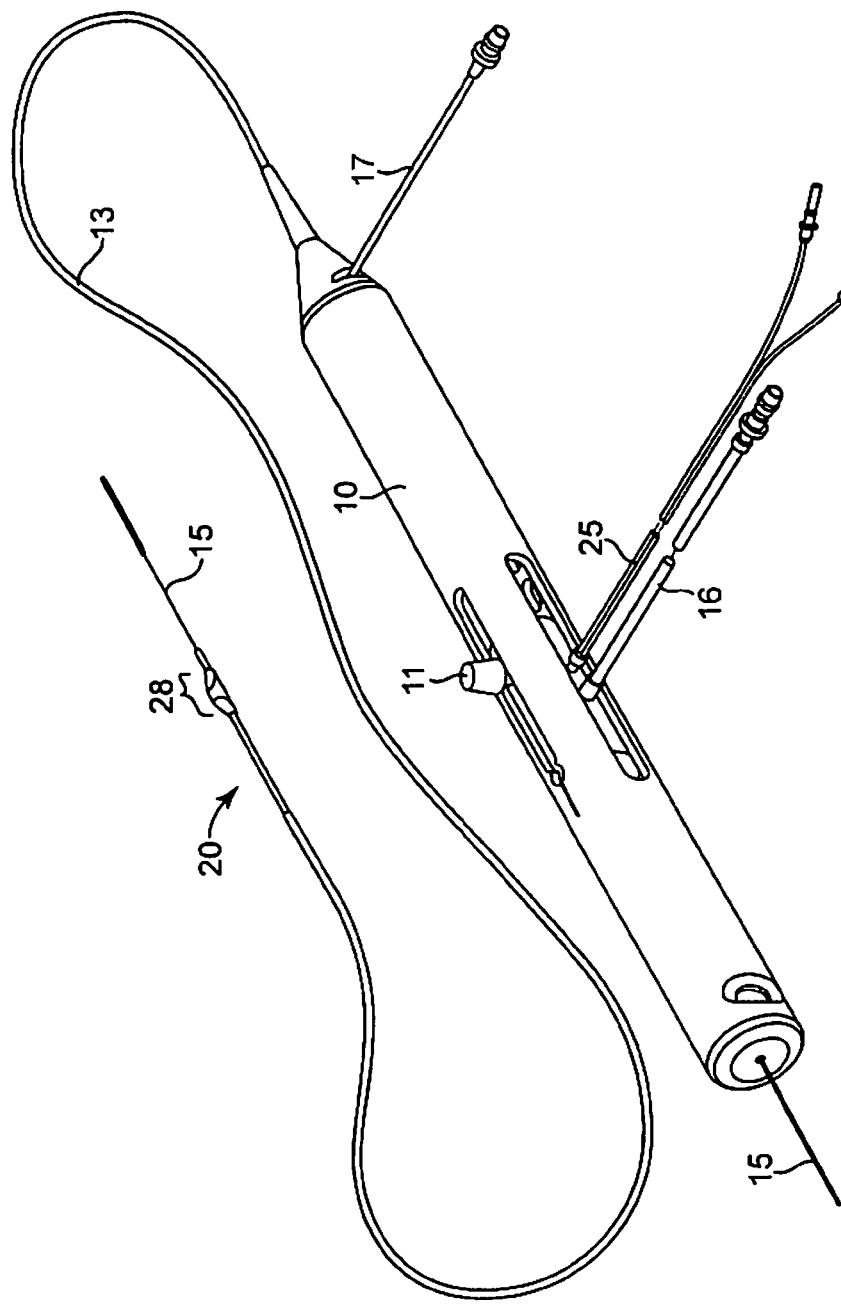
FIG. 1 is an isometric drawing of an exemplary rotational atherectomy device.

FIG. 1 illustrates one embodiment of a rotational atherectomy device according to the disclosure of commonly assigned U.S. patent application Ser. No. 11/761,128. The device includes a handle portion 10, an elongated, flexible drive shaft 20 having an eccentric enlarged abrading head 28, and an elongated catheter 13 extending distally from the handle portion 10. The drive shaft 20 is constructed from helically coiled wire as is known in the art and the abrading head 28 is fixedly attached thereto. The catheter 13 has a lumen in which most of the length of the drive shaft 20 is disposed, except for the enlarged abrading head 28 and a short section distal to the enlarged abrading head 28. The drive shaft 20 also contains an inner lumen, permitting the drive shaft 20 to be advanced and rotated over a guide wire 15. A fluid supply line 17 may be provided for introducing a cooling and lubricating solution (typically saline or another biocompatible fluid) into the catheter 13.

The handle 10 desirably contains a turbine (or similar rotational drive mechanism) for rotating the drive shaft 20 at high speeds. The handle 10 typically may be connected to a power source, such as compressed air delivered through a tube 16. A single fiber optic cable or a pair of fiber optic cables 25 may also be provided for monitoring the speed of rotation of the turbine and drive shaft 20. The handle 10 also desirably includes a control knob 11 for advancing and retracting the turbine and drive shaft 20 with respect to the catheter 13 and the body of the handle.

In general, details regarding such handles and associated instrumentation are well known in the industry, and are described in for example, U.S. Pat. No. 5,314,407, issued to Auth. The remainder of this disclosure is dedicated to the abrading head 28, and variations thereof.

Figure 2:
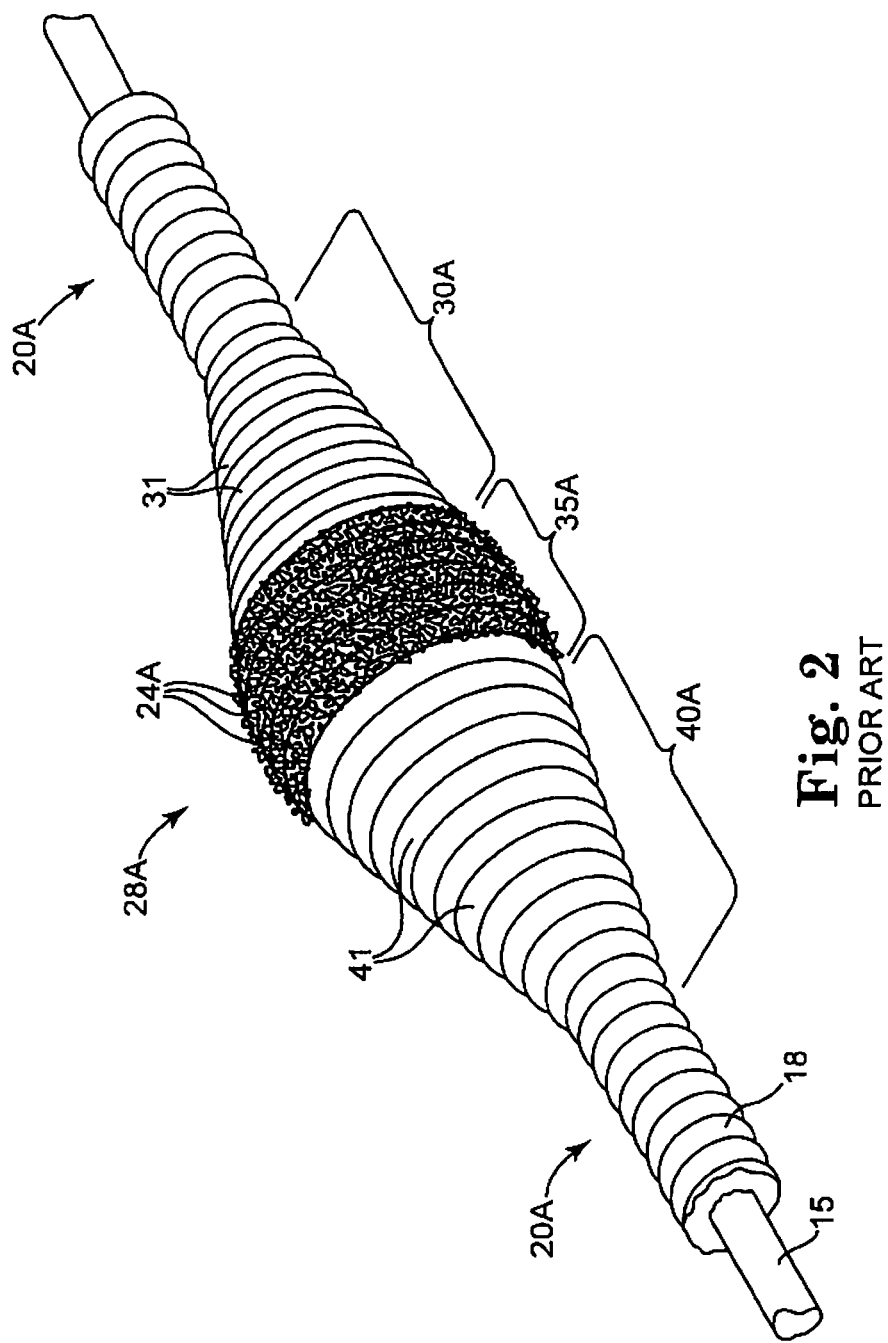
FIG. 2 is a perspective, broken-away view of a known, flexible eccentric cutting head formed from the drive shaft.
Figure 3:
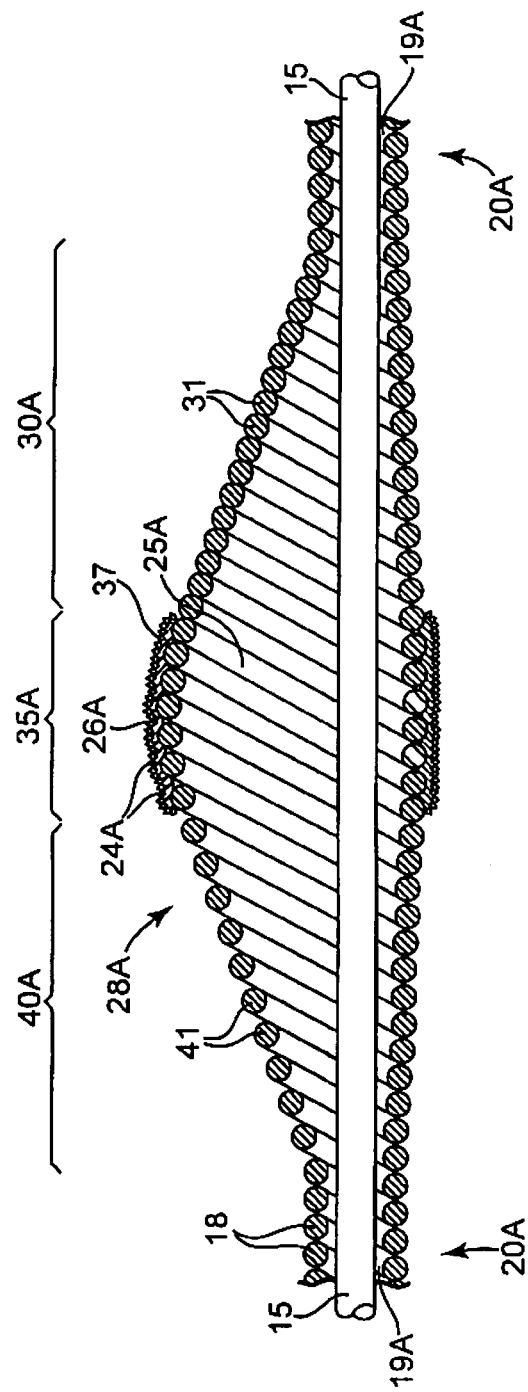
FIG. 3 is a broken-away, longitudinal cross-sectional view of a known, eccentric cutting head formed from the drive shaft.
Figure 4:
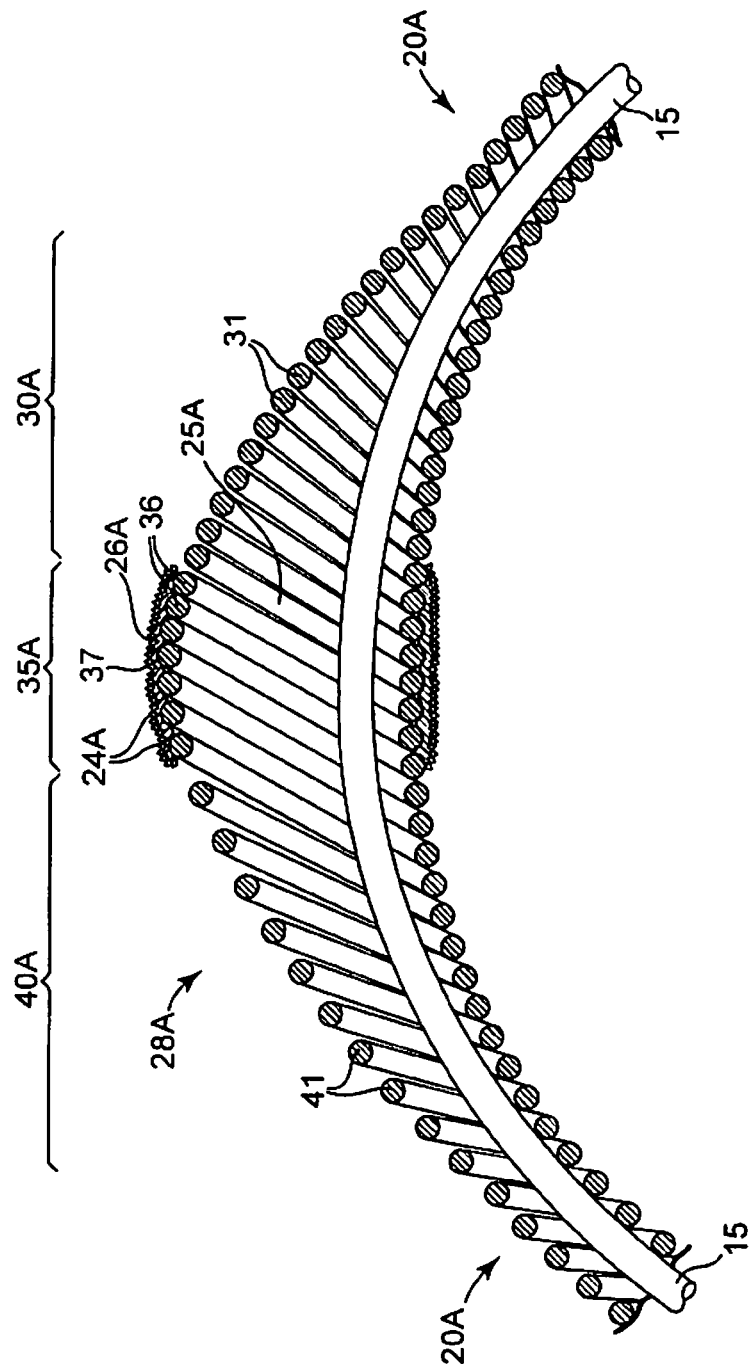
FIG. 4 is a broken-away, longitudinal cross-sectional view illustrating the flexibility of a known, flexible eccentric enlarged cutting head formed from the drive shaft.

FIGS. 2-4 illustrate details of a known, eccentric, enlarged-diameter abrading section 28A of a drive shaft 20A. The drive shaft 20A includes one or more helically wound wires 18 which define a guide wire lumen 19A and a hollow cavity 25A within the enlarged abrading section 28A. Except for the guide wire 15 traversing the hollow cavity 25A, the hollow cavity 25A is substantially empty. The eccentric enlarged diameter abrading section 28A includes, relative to the location of the stenosis, proximal 30A, intermediate 35A and distal 40A portions. Wire turns 31 of the proximal portion 30A of the eccentric enlarged diameter section 28A preferably have diameters that progressively increase distally at a generally constant rate, thereby forming generally the shape of a cone. Wire turns 41 of the distal portion 40A preferably have diameters that progressively decrease distally at a generally constant rate, thereby forming generally the shape of a cone. Wire turns 36 of the intermediate portion 35A are provided with gradually changing diameters to provide a generally convex outer surface which is shaped to provide a smooth transition between the proximal and distal conical portions of the enlarged eccentric diameter section 28A of the drive shaft 20A.

Continuing with the known device of FIGS. 2-4, at least part of the eccentric enlarged diameter abrading section of the drive shaft 28A (preferably the intermediate portion 35A) includes an external surface capable of removing tissue. A tissue removing surface 37 with a coating of an abrasive material 24A that defines a tissue removing segment of the drive shaft 20A is shown attached directly to the wire turns of the drive shaft 20A by a suitable binder 26A.

FIG. 4 illustrates the flexibility of the known eccentric enlarged diameter abrading section of the drive shaft 28A, shown with drive shaft 20A advanced over guide wire 15. In the embodiment shown, adjacent wire turns of the intermediate portion 35A of the eccentric enlarged cutting head of the drive shaft are secured to one another by the binding material 26A securing the abrasive particles 24A to the wire turns 36. Proximal portion 30A and distal 40A portion of the eccentric enlarged diameter section of the drive shaft includes wire turns 31 and 41, respectively, are not secured to one another, thereby permitting such portions of the drive shaft to flex, as shown in the drawing. Such flexibility facilitates advancement of the device through relatively tortuous passageways and, in some embodiments, flexing of the eccentric enlarged diameter abrading section 28A during high-speed rotation. Alternatively, adjacent wire turns 36 of the intermediate portion 35A of the eccentric enlarged diameter abrading section 28A of the drive shaft may be secured to one another, thereby limiting the flexibility of abrading section 28A.

Figure 5:
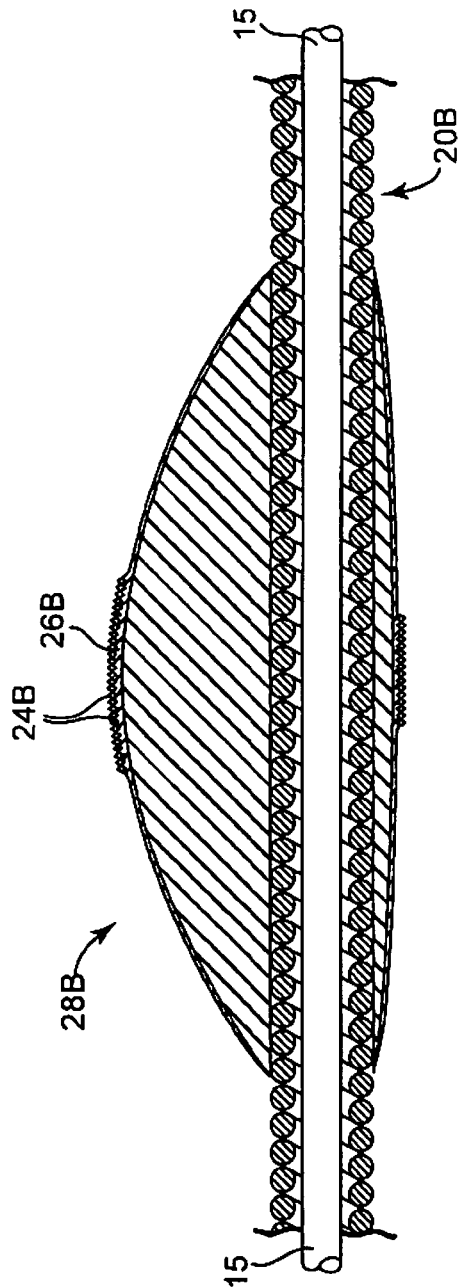
FIG. 5 is a longitudinal cross-sectional view of a known solid and inflexible eccentric abrasive burr attached to a drive shaft.

FIG. 5 illustrates another known rotational atherectomy device which employs a solid asymmetrical abrasive burr 28B attached to a flexible drive shaft 20B, rotated over a guide wire 15, such as disclosed in U.S. Pat. No. 5,681,336, issued to Clement. The drive shaft 20B may be flexible, however the solid asymmetrical abrasive burr 28B is inflexible. The eccentric tissue removing burr 28B has a coating of abrasive particles 24B secured to a portion of its outer surface by a suitable binding material 26B. This construction has limited utility, however because, as Clement explains at Column 3, Lines 53-55, the asymmetrical burr 28B must be rotated at "lower speeds than are used with high speed ablation devices, to compensate for heat or imbalance." That is, given both the size and mass of the solid burr-type construction, it is infeasible to rotate such a burr at the high speeds used during atherectomy procedures, i.e., 20,000-200,000 rpm.

Figure 6:
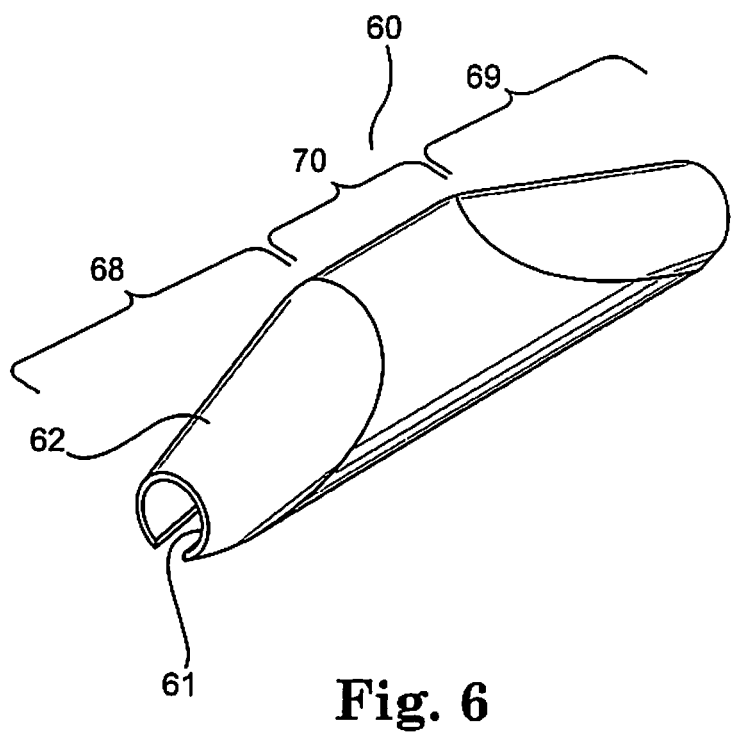
FIG. 6 is an isometric drawing of an eccentric abrading head.
Figure 7:
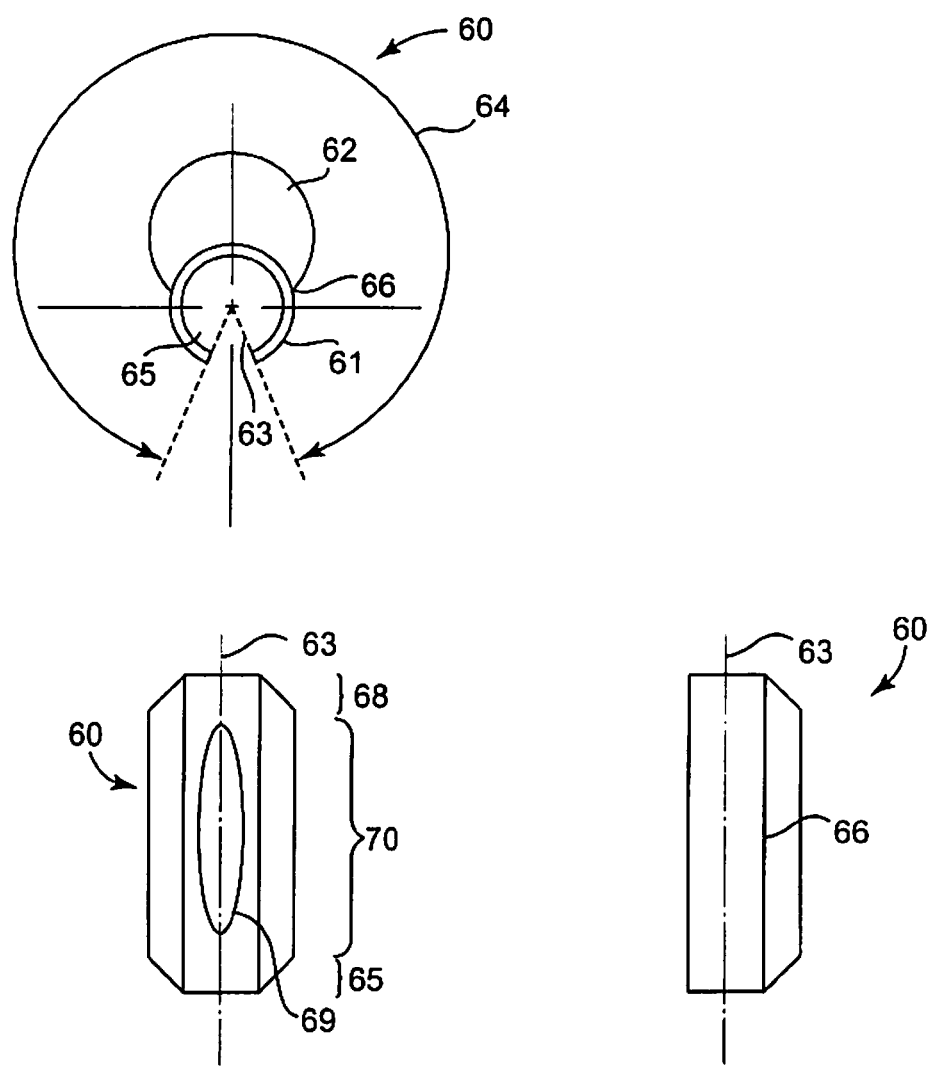
FIG. 7 is an orthographic projection drawing of the eccentric abrading head of FIG. 6.

FIGS. 6 and 7 illustrate an exemplary embodiment of an eccentric abrading head 60, formed as a bi-metal crown assembly. The abrading head 60 includes a relatively low density metal in the portion closest to the center of rotation of the drive shaft, and a relatively high density metal in the portion farthest away from the center of rotation of the drive shaft. Compared to a similar crown geometry made only from a single metal, the bi-metal crown has a higher fraction of its mass located away from the center of rotation, and therefore has a larger rotational inertia, and a larger separation between the center of mass and the center of rotation of the drive shaft. In addition, the mass of a bi-metal crown, compared to a similarly-sized single-metal crown, may be slightly more or slightly less, depending on the densities of the specific metals chosen for the crown; the mass of the bi-metal crown may be substantially greater than if voids or holes were inserted into the single-metal crown, in an effort to reposition the center of mass.

Because the center of mass is moved farther away from the center of rotation, there may be a greater displacement of the crown during rotation of the drive shaft due to centrifugal force, for a particular rotational speed. More specifically, the abrasive portion of a multi-metal abrading head may trace out a larger cylinder than that of a single-material external abrading head with a comparable size and shape. (Note that in some embodiments, such an abrading cylinder may be circular in cross-section. Alternatively, the cross-section of the abrading cylinder may be elliptical, or may have any other suitable regular or irregular shape, corresponding to orbital motion.) This larger abrading cylinder for the bi-metal head, compared to a single-metal head, may have several advantages.

First, in order to achieve a particular desired abrading cylinder size, the rotation speed of the drive shaft may be reduced. This may result in less complicated and less expensive mechanical components for the drive shaft motor, and possibly less incidental damage to tissue in the vessel that is being cleaned.

Second, in order to achieve a particular desired abrading cylinder size, the rotation speed may be unchanged, but the size of the abrading head itself may be reduced. Using a smaller head may be particularly desirable when feeding the head through the torturous blood vessel passageways inside the body. In addition to making it easier to get to the stenosis location, a reduced-size bi-metal head may be able to fit inside particularly tight locations that were previously unreachable with a single-metal head.

An exemplary material for the low density metal may be stainless steel. Stainless steel may vary in composition, but generally has a density in the range of about 7.6 to 8.1 grams per cubic centimeter. For instance, MIM-316L may have a density of about 7.80 g/cm$^3$, 304L may have a density of about 7.75 g/cm$^3$, MIM-17-4 PH (as sintered) may have a density of about 7.60 g/cm$^3$, MIM-17-4-PH Heat-treated (H900) may have a density of about 7.60 g/cm$^3$, 420 may have a density of about 7.70 g/cm$^3$, and so forth. In general, a commonly quoted value for the density of steel is 7.7 g/cm$^3$.

Stainless steel is generally considered to be a relatively strong material, so that the connection portion of the crown, which wraps all or partially around the drive shaft, may have a relatively thin wall thickness. This may be desirable, in that most of the material in the crown may be located on only one side of the center of rotation, thereby reducing any counter-weight effects.

An exemplary material for the high density metal may be tungsten or tantalum. Tungsten has a room-temperature density of about 19.25 g/cm$^3$, and tantalum has a room-temperature density of about 16.69 g/cm$^3$. Both of these materials are over twice as dense as stainless steel.

It will be understood that the specific materials cited above are merely exemplary, and that other relatively low- and high-density metals may be used as well.

In the exemplary embodiment of FIGS. 6 and 7, the abrading head 60 includes two portions, a connecting portion 61 and an eccentric portion 62, each made from a different material. Both of these are described in detail below.

The connecting portion 61 of FIGS. 6 and 7 is in the form of an incomplete cylinder, made from a low-density metal and generally concentric with the rotation axis 63 of the drive shaft. The connecting portion 61 partially surrounds a portion of the drive shaft, and is fixedly attached to the drive shaft by any suitable method, such as welding, so that when the drive shaft rotates, the connecting portion 61 rotates with it.

The connecting portion 61 may be manufactured from a cylindrical tube with an inner diameter that is sized to match the outer dimension of the coiled wire of the drive shaft, so that a longitudinal portion of the drive shaft fits snugly inside the connecting portion 61. A longitudinal slice of the complete cylindrical tube may be cut away during the manufacturing process, so that the remaining incomplete cylinder may have a cross-section that is generally invariant along most or all of the longitudinal extent of the connecting portion 61.

The amount of material removed from the complete cylinder to form the incomplete cylinder may be measured by an azimuthal angle 64, which would be 360 degrees if the tube were left complete, would be 180 degrees if the tube were cut completely in half, and so forth. In general, it is desirable to include more than half the tube, so that there is some mechanical support for "holding onto" the drive shaft, but less than 360 degrees to simplify the ease in attaching the connection portion 61 to the drive shaft. Any suitable azimuthal angle may be used, including but not limited to 360 degrees, 270 degrees, 260 degrees, 252 degrees, 250 degrees, 240 degrees, 230 degrees, 225 degrees, 220 degrees, 210 degrees, 200 degrees, the range of 240 degrees to 270 degrees, the range of 180 to 360 degrees, or any other suitable value.

In some embodiments, the connecting portion 61 includes a hole, aperture or slot 65 opposite the opening, through which the connecting portion 61 may be attached to the eccentric portion 62. The connecting and eccentric portions 61 and 62 may be attached by any of a variety of known methods, including welding, soldering, brazing, mechanical swaging, and so forth. The welding or other attachment method may occur through the hole 65 mentioned above, and/or along a line 66, 67 adjacent to either or both longitudinal edges of the connecting portion 61.

In some embodiments, the outer dimension of the coiled wire of the drive shaft remains roughly constant along the portion of the drive shaft that fits within the crown; in other words, in these embodiments, the drive shaft coils do not increase in size, then decrease in size along the length of the crown, but remain constant in size throughout. In other embodiments, the outer dimension of the coiled wire of the drive shaft do vary along the longitudinal extent of the abrading head 60, as in, for example, the known abrading head of FIG. 3. In those embodiments, the connecting portion 61 may not be truly cylindrical, and may have an inner surface that matches the outer surface of the drive shaft in order to achieve a snug fit.

The eccentric portion 62 of FIGS. 6 and 7 is in the form of a generally solid piece of high-density metal, although there may optionally be one or more hollow portions or voids in the eccentric portion 62.

The eccentric portion 62 may be divided into three sections. In the proximal and distal sections 68 and 69 (at the longitudinal ends of the crown), the radial extent (or cross-sections) increase with an increase in longitudinal distance from the longitudinal ends of the crown. In the central section 70 (the longitudinal middle of the abrading head 60), the radial extent (or cross-section) remains roughly constant, as a function of longitudinal distance along the abrading head 60. In the proximal and distal sections 68 and 69, the change in radial extent may be roughly linear throughout. The slope of the distal section 69 may be equal to or different from that in the proximal 68 section. Alternatively, the proximal and/or distal sections may be curved in total or in portions. The curvature may be convex and/or concave. The curvature of the distal section may be equal to or different from that in the proximal section.

The outermost surfaces of the proximal, central, and/or distal portions 68, 70, 69 of the eccentric portion 62 may be coated with an abrasive material. Typically, as the abrading head 60 is being directed toward the site of the stenosis, the distal portion 69 may be used to remove plaque when passing through a small vessel, effectively boring a way through the plaque for the rest of the instrument. Once the abrading head 60 is located at the site of the stenosis, much of the actual plaque removal is done by the abrasive material on the central portion 70, because the central portion extends farthest away from the rotation axis 63 of the drive shaft during operation.

The abrasive material may be any suitable material, such as diamond powder, fused silica, titanium nitride, tungsten carbide, aluminum oxide, boron carbide, or other ceramic materials. Preferably the abrasive material includes diamond chips (or diamond dust particles) attached directly to the tissue removing surface(s) by a suitable binder; such attachment may be achieved using known techniques, such as conventional electroplating or fusion technologies (see, for example, U.S. Pat. No. 4,018,576). Alternately the abrasive portions of the burrs may comprise mechanically or chemically roughening the external surface(s) of one or more of the burrs. In yet another variation, the external surface may be etched or cut (e.g., with a laser) to provide small but effective abrading surfaces. Other similar techniques may also be utilized to provide a suitable surface for removing tissue.

The shape of the eccentric portion 62, and/or distribution of high-density metal therein, may be such that all or nearly all of the high-density metal may be located entirely on one side of the center of rotation of the drive shaft. This arrangement creates a large amount of eccentric mass, and desirably shifts the center of mass of the crown away from the center of rotation of the drive shaft, resulting in eccentric motion of the crown when rotated at high speed, wherein the crown is displaced from the rotational axis of the drive shaft 63.

Figure 8:
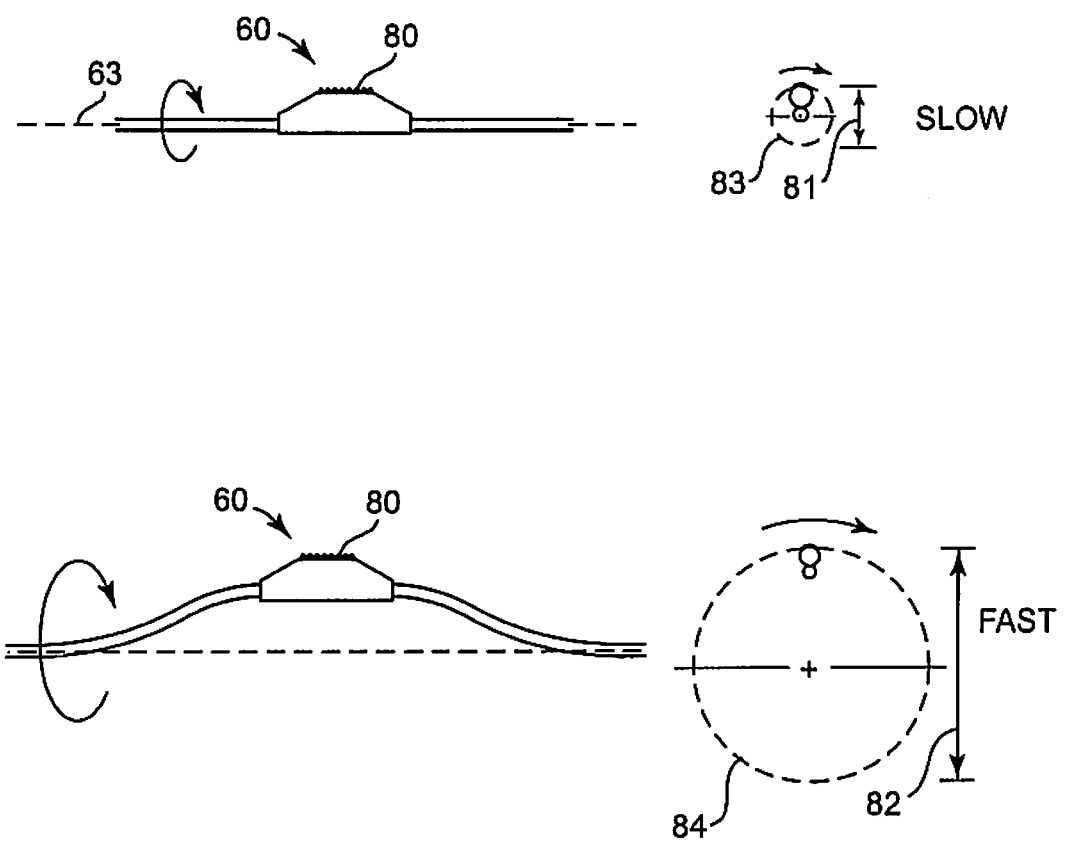
FIG. 8 is a schematic drawing of the abrading cylinders at slow and fast drive shaft rotational velocities.

FIG. 8 is a schematic drawing of the abrading cylinders, formed by the abrasive portion 80 of the central portion 70 of the abrading head 60, as the drive shaft is rotated at relatively slow and relatively fast rotational velocities. At "slow" speeds, the drive shaft remains essentially straight through the abrading head 60, and rotates generally about its axis of rotation without significant deformation. This is concentric motion. At these slow speeds, the size 81 of abrading cylinder 83 is roughly twice the distance from the axis of rotation to the abrasive portion 80. At "high" speeds, the abrading head 60 experiences a significant centrifugal force that forces it away from the rotational axis of the drive shaft as it spins, and the drive shaft deforms in the region of the abrading head 60 under the influence of this centrifugal force. At these high speeds, the size 82 of the abrading cylinder 84 also includes the deformation of the drive shaft due to centrifugal force. The size 82 of the abrading cylinder 84 at high speeds may therefore be larger than the size 81 of the abrading cylinder 83 at low speeds. This is eccentric motion of the abrading head 60, also referred to as orbital motion.

In practical terms, this means that the abrading head may be inserted into the vessel and directed to the stenosis while the drive shaft is stopped or is rotating at low speeds. Once the abrading head is in position at the stenosis, the drive shaft may be rotated quickly, and the abrading cylinder may be increased well beyond the size of the abrading head itself. Once the stenosis is removed, the drive shaft may be slowed or stopped, and the abrading head may be retracted.

In FIGS. 6 and 7, the eccentric portion 62 is a solid piece of material, with no hollow portions or voids anywhere inside. The center of mass of the eccentric portion 62 lies within the eccentric portion 62 itself, and is therefore laterally separated from the rotational axis 63 of the drive shaft.

In contrast, the connecting portion 61 is largely concentric and well centered about the rotational axis 63 of the drive shaft, so that the center of mass of the connecting portion 61 may be quite close to the rotational axis 63. If the connecting portion 61 were a true, complete cylinder, then the center of mass of the connecting portion 61 would lie exactly on the rotational axis 63 of the drive shaft. As the cylinder becomes more incomplete, the center of mass shifts slightly off-axis. In the extreme case of an azimuthal angle of 0 degrees (just an impractically small, thin stripe of material), then center of mass would be displaced from the rotational axis 63 by the radius of the drive shaft. For the purposes of this document, we neglect the slight shift off-axis of the center of mass, due to the incompleteness of the cylinder, and say that the connecting portion 61, in the embodiment of an incomplete cylinder, has its center of mass that is concentric with the rotational axis 63 of the drive shaft.

Because the connecting portion 61 is formed from a less dense material than the eccentric portion 62, the center of mass of the combination of the two lies farther off axis than if the connecting portion 61 were made from the same high-density material as the eccentric portion 62. This is advantageous, and provides a desirably increased separation between the center of mass of the abrading head 60 and the rotational axis 63 of the drive shaft.

The precise geometry of the connecting portion 61 and eccentric portion 62 may vary somewhat from the embodiment shown in FIGS. 6 and 7. These variations in geometry are discussed below, with the implicit assumption that one of ordinary skill in the art may readily adapt the embodiment of FIGS. 6 and 7 to the variations below.

The embodiment of FIGS. 6 and 7 show solid connecting portion 61 and solid eccentric portion 62, each made of a single material. As an alternative, the eccentric portion and/or connecting portion may include more than one layer. Each layer may be made from its own material with its own density. The material of any particular layer may or may not be the same as any other layer. The layers may increase in density, from inside to outside, may alternate in density, or follow a different pattern entirely. The layers may be nested in shape, with each layer completely or partially surrounding the adjacent layer beneath it. Alternatively, the layers may have a different pattern in shape. The layers may be of equal thickness, or of different thickness, or of thickness that varies within each layer.

In some embodiments, the layers of the connection portion and/or the eccentric portion may be formed so that the center of mass is displaced laterally from the rotational axis of the drive shaft, while the external profile of the eccentric portion is symmetric, with respect to the rotational axis. This may occur with a plurality of asymmetric layers inside the eccentric and/or connecting portions, with an asymmetric distribution of mass on one side of the rotation axis versus the other. There may also be hollow portions, voids and/or holes inside either portion to redistribute the mass. When the outer profile of the eccentric portion is symmetric with respect to the rotation axis of the drive shaft, the eccentric portion may be referred to as a "non-eccentric" portion.

In some embodiments, the connecting portion has an exterior face that is non-concentric with the rotational axis of the drive shaft, and the non-eccentric portion has an interior face matched to the exterior face of the connection portion.

In some embodiments, the non-eccentric portion includes a plurality of layers formed from a plurality of materials. At least two materials in the plurality have different densities. At least one layer in the plurality has an exterior face that is non-concentric with the rotational axis of the drive shaft.

In some embodiments, the non-eccentric portion has an exterior face that is concentric with the rotational axis of the drive shaft. The at least one non-eccentric abrading head has a center of mass that is laterally separated from the rotational axis of the drive shaft.

The description of the invention and its applications as set forth herein is illustrative and is not intended to limit the scope of the invention. Variations and modifications of the embodiments disclosed herein are possible, and practical alternatives to and equivalents of the various elements of the embodiments would be understood to those of ordinary skill in the art upon study of this patent document. These and other variations and modifications of the embodiments disclosed herein may be made without departing from the scope and spirit of the invention.

We claim:

1. A high-speed rotational atherectomy device for opening a stenosis in an artery having a given diameter, comprising: a guide wire having a maximum diameter less than the diameter of the artery; a flexible, elongated, rotatable drive shaft advanceable over the guide wire, the drive shaft having a rotational axis and having a controllable drive shaft rotation speed; at least one eccentric abrading head comprising a geometric eccentricity and a center of mass radially offset from the rotational axis of the drive shaft, wherein the at least one eccentric abrading head is attached to the drive shaft, and comprising:

a connecting portion fixedly attached to and at least partially surrounding the drive shaft, the connecting portion attached to the drive shaft and being formed from a connecting portion material, wherein the connecting portion is an incomplete cylinder having a center of mass that is concentric with the rotational axis of the drive shaft;

an eccentric portion fixedly attached to and at least partially surrounding the connecting portion and formed from an eccentric portion material different from the connecting portion material, the eccentric portion including a proximal portion, a central portion adjacent to the proximal portion, and a distal portion adjacent to the central portion opposite the proximal portion; and an abrasive portion disposed on an exterior surface of the central portion; wherein the eccentric portion material is more dense than the connecting portion material, and wherein the center of mass of the at least one eccentric abrading head is radially offset from the rotational axis of the drive shaft as a result of a combination of the geometric eccentricity of the at least one eccentric abrading head and the more dense material of the eccentric portion.

2. The high-speed rotational atherectomy device of claim 1, wherein the eccentric portion has a center of mass that is laterally separated from the rotational axis of the drive shaft.

3. The high-speed rotational atherectomy device of claim 1, wherein the central portion has a cross-section that is generally invariant along the longitudinal extent of the central portion.

4. The high-speed rotational atherectomy device of claim 1, wherein the connecting portion is an incomplete cylinder having an inner diameter matched to an outer diameter of the drive shaft.

5. The high-speed rotational atherectomy device of claim 1, wherein the connecting portion has a generally annular cross-section that subtends an azimuthal angle between 180 degrees and 360 degrees.

6. The high-speed rotational atherectomy device of claim 5, wherein the connecting portion has a generally annular cross-section that subtends an azimuthal angle between 240 degrees and 270 degrees.

7. The high-speed rotational atherectomy device of claim 1, wherein the eccentric portion is disposed entirely on one side of the rotational axis of the drive shaft.

8. The high-speed rotational atherectomy device of claim 1, wherein the connecting portion includes an aperture for attaching to the eccentric portion.

9. The high-speed rotational atherectomy device of claim 1, wherein the eccentric portion is attached to the connecting portion along two longitudinal edges of the eccentric portion.

10. The high-speed rotational atherectomy device of claim 1,
wherein the connecting portion material is stainless steel; and
wherein the eccentric portion material is tungsten.

11. The high-speed rotational atherectomy device of claim 1,
wherein the connecting portion material is stainless steel; and
wherein the eccentric portion material is tantalum.

12. The high-speed rotational atherectomy device of claim 1,
wherein the abrasive portion traces out a low-speed abrading cylinder as the drive shaft is rotated at a low angular velocity;
wherein the abrasive portion traces out a high-speed abrading cylinder as the drive shaft is rotated at a high angular velocity; and
wherein the high-speed abrading cylinder is larger than the low-speed abrading cylinder.

13. The high-speed rotational atherectomy device of claim 1, wherein the proximal and distal portions have cross-sections that decrease in size with longitudinal distance away from the central portion.

14. The high-speed rotational atherectomy device of claim 13 wherein the proximal and distal portions have cross-sections that decrease linearly in size with longitudinal distance away from the central portion.

15. The high-speed rotational atherectomy device of claim 1, wherein the eccentric portion comprises a single layer made from a single material.

16. The high-speed rotational atherectomy device of claim 1, wherein the eccentric portion comprises a plurality of layers made from a plurality of materials having a plurality of densities.

17. A method for opening a stenosis in an artery having a given diameter, comprising:
providing the high-speed rotational atherectomy device as recited in claim 1;
advancing the guide wire into the artery to a position proximal to the stenosis;
advancing the drive shaft over the guide wire wherein the at least one eccentric abrading head is adjacent the stenosis;
rotating the drive shaft and attached at least one eccentric abrading head at a speed between 20,000 and 200,000 rpm;
creating an orbital path traversed by the at least one eccentric abrading head; and
abrading the stenosis with the at least one eccentric abrading head.

18. The method of claim 17, further comprising:
rotating the drive shaft and attached at least one eccentric abrading head at a relatively low speed;
tracing out a low-speed abrading cylinder with the abrasive portion as the at least one eccentric abrading head is rotated at a relatively low speed;
rotating the drive shaft and attached at least one eccentric abrading head at a relatively high speed; and
tracing out a high-speed abrading cylinder with the abrasive portion as the at least one eccentric abrading head is rotated at a relatively high speed;

wherein the high-speed abrading cylinder is larger than the low-speed abrading cylinder.

* * * * *